United States Patent [19]
Malenchek et al.

[11] Patent Number: 5,980,494
[45] Date of Patent: Nov. 9, 1999

[54] SAFETY SYRINGE

[75] Inventors: Robert Malenchek, 279 Sunnymead Rd., Somerville, N.J. 08876; Edwin Bolz, Chester, N.Y.

[73] Assignee: Robert Malenchek, Somerville, N.J.

[21] Appl. No.: 08/995,640

[22] Filed: Dec. 22, 1997

[51] Int. Cl.$^6$ .................................................. A61M 5/32
[52] U.S. Cl. ........................................ 604/198; 604/110
[58] Field of Search .................................. 604/110, 192, 604/198, 263

[56] References Cited

U.S. PATENT DOCUMENTS

| | | | |
|---|---|---|---|
| 5,057,079 | 10/1991 | Tiemann et al. | 604/110 |
| 5,279,584 | 1/1994 | Dillard, III et al. | 604/198 |
| 5,312,370 | 5/1994 | Talonn et al. | 604/198 |
| 5,415,645 | 5/1995 | Friend et al. | 604/110 |
| 5,573,513 | 11/1996 | Wozencroft | 604/198 |

*Primary Examiner*—Corrine McDermott
*Attorney, Agent, or Firm*—Omri M. Behr, Esp.

[57] ABSTRACT

A thermoplastic molded housing has a cylindrical bore with axial grooves and inclined camming surfaces extending about the bore surface. A plastic molded vial for receiving injectable fluid in a cavity receives a plunger therein for dispensing the fluid and for displacing the vial. The vial has a ratchet member with fixed ratchet teeth and tabs about its circumference which tabs and teeth form camming surfaces which cooperate with the housing camming surfaces. The tabs are aligned for reciprocating in the housing bore grooves. A ring is secured captured to the vial for rotation about the vial and for limited axial displacement along the vial longitudinal axis. A spring urges the ring and vial to the retracted position. The ring has tabs with camming surfaces for selectively engaging the grooves and the camming surfaces of the ratchet member tabs, ratchet teeth and housing bore camming surfaces to selectively position the vial and the needle attached thereto from a needle retracted position enclosed by the housing bore to an extended needle use position and for retracting the needle and vial to a permanent retracted position in response to depression of the plunger and vial or displacement of the vial alone and to the spring force on the ring.

28 Claims, 10 Drawing Sheets

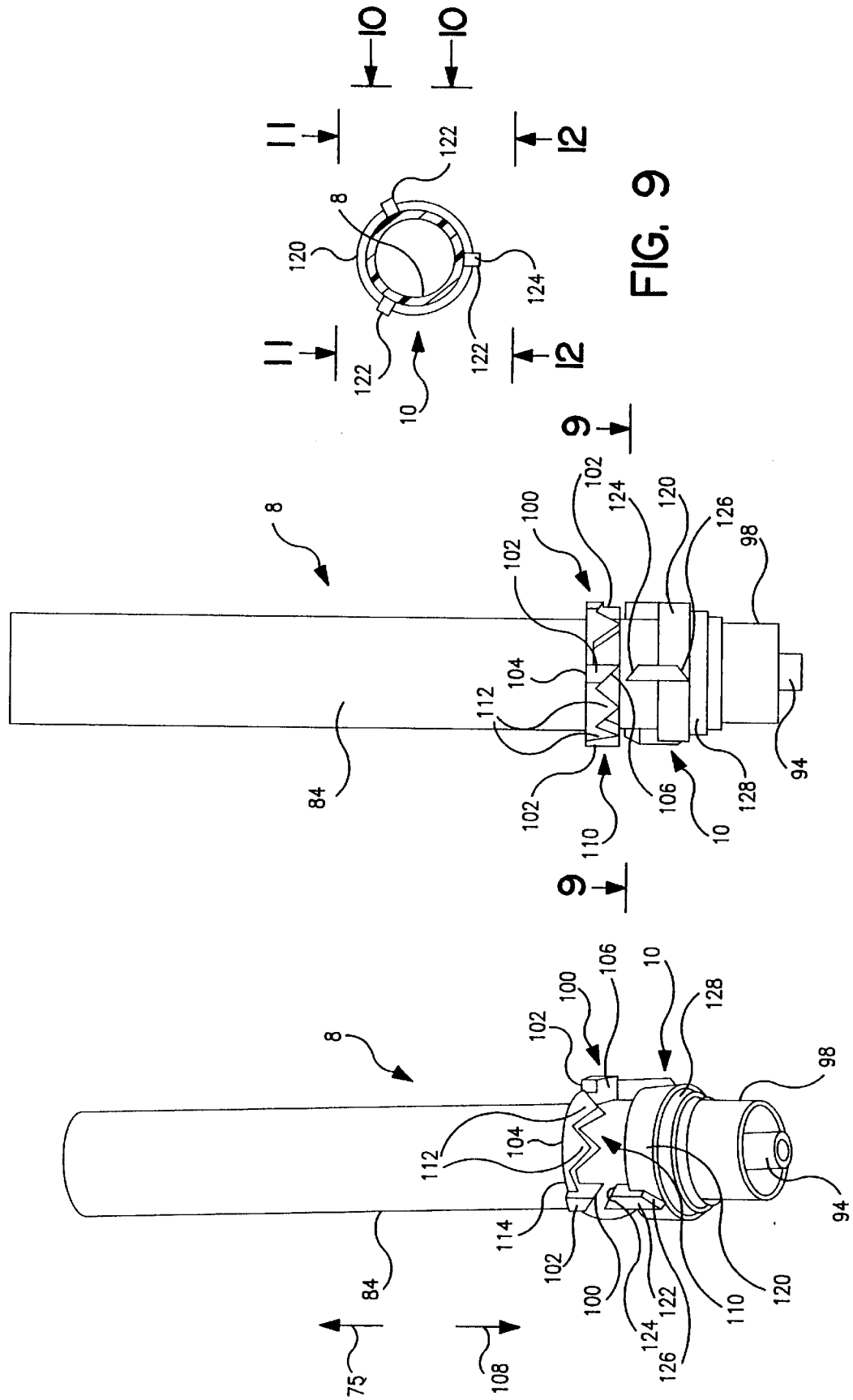

POSITION 1

POSITION 2

POSITION 3

SAFETY SYRINGE

FIELD OF THE INVENTION

This invention relates to safety syringes including a cylindrical housing with a bore, a plunger in the bore, a needle coupled to the housing and in fluid communication with the bore and safety devices for retracting the needle into the bore after use.

DISCUSSION OF THE PRIOR ART

The need for a syringe that automatically extends and retracts its needle upon axial displacement of the syringe plunger providing a relatively simply operation for permanently securing the needle in the housing bore while temporarily securing the needle within the bore prior to use of the syringe, has long been recognised. Numerous solutions to this problem have been offered, including those by applicant. Heretofore however a solution to the problem has not been offered which permits the needle to be retracted into the bore when the liquid within the syringe has not been completely expelled, nor have the previous solution been sufficiently inexpensive in production to permit their widespread adoption.

SUMMARY OF THE INVENTION

A safety syringe according to the present invention comprises a housing having a bore extending in an axial direction from a proximal housing end to a distal end. A vial has a fluid receiving chamber for receiving a plunger and has proximal and distal ends, the vial for axial displacement in the housing bore between retracted and extended positions. The distal vial end secures a needle thereto in fluid communication with the vial chamber, the needle being fully retracted in the bore when the vial is retracted and extending from the bore distal end when the vial is extended.

Resilient means resiliently urge the vial to the retracted position. Positioning means responsive to an initial vial axial displacement releasably lock the vial in the extended position, the positioning means for unlocking the vial upon a subsequent vial axial displacement and for displacing the vial to the retracted position in response to said unlocking.

In one aspect, a plunger in the vial chamber displaces the vial axially.

In a further aspect the positioning means include cam means secured to the vial and housing bore responsive to the axial position of the vial in the bore for causing releasable locking, unlocking and permanently locking of the vial in the extended and retracted positions.

In a further aspect the cam means comprises cooperative ratchet and pawl means.

In a still further aspect the ratchet and pawl means includes ratchet teeth on the housing in the bore, a pawl rotatably secured to the vial for releasable engagement with the housing teeth and cam means on the vial for selective engagement and camming displacement of the pawl relative to the ratchet teeth during the initial and subsequent axial displacements.

In a further aspect guide means axially guide the vial during the displacement.

In a further aspect the ratchet means comprises ratchet teeth on the housing in the bore adjacent the distal end and ratchet teeth externally on the vial distal end and a pawl with a camming surface rotatably secured to the vial, the resilient means for resiliently urging the pawl in selective engagement with the vial and housing ratchet teeth in response to the axial displacement of the vial to the bore distal end.

In a still further aspect the guide means includes an axially extending groove in the housing bore and a guide tab secured to the vial engaged with the grooves. The ratchet means includes a tab on the vial with a first cam surface, the housing bore having first and second axial grooves, one of the grooves for axially guiding the tab during the vial displacement, a pawl rotatably secured to the vial having a second cam surface, the pawl being in the one groove in the initial retracted position and being cammed into engagement with the vial and housing ratchet teeth by the first cam surface.

In a further aspect the vial ratchet teeth are for camming the pawl out of engagement with the housing ratchet teeth from the extended position into engagement with the second groove for retracting the vial to the second retracted position in response to the urging.

In a further aspect the tab and pawl locking means are coupled to the second groove at the housing bore proximal end for locking the vial retracted.

BRIEF DESCRIPTION OF THE DRAWINGS

FIGS. 7 and 8 are respective more detailed isometric and elevation views of the vial of FIG. 4 with a camming ring attached;

FIG. 9 is a sectional plan view of the embodiment of FIG. 8 taken along lines 9—9;

DESCRIPTION OF THE PREFERRED EMBODIMENTS

Figure 1:
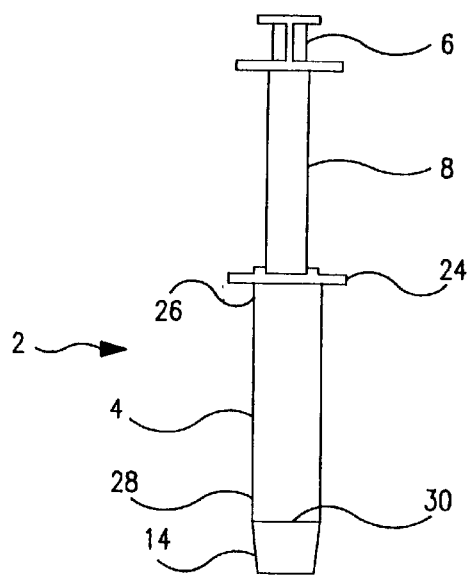
FIG. 1 is an elevation view of a syringe according to the present invention.
Figure 3:
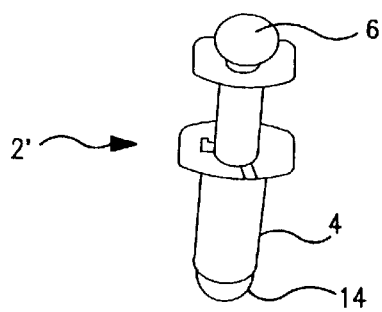
FIG. 3 is an isometric view of the syringe of FIG. 1.

In FIGS. 1–6, syringe 2 comprise a thermoplastic molded housing 4, a thermoplastic molded plunger 6 of conventional configuration, a thermoplastic molded vial 8, a thermoplastic camming vial positioning ring 10 rotatably and axially movably secured and captured to the vial 8, a compression coil spring 12 and a cap 14 ultrasonically or heat welded or otherwise permanently bonded and secured to the housing 4. A needle assembly 36 is releasably secured to the vial 8

Figure 1A:
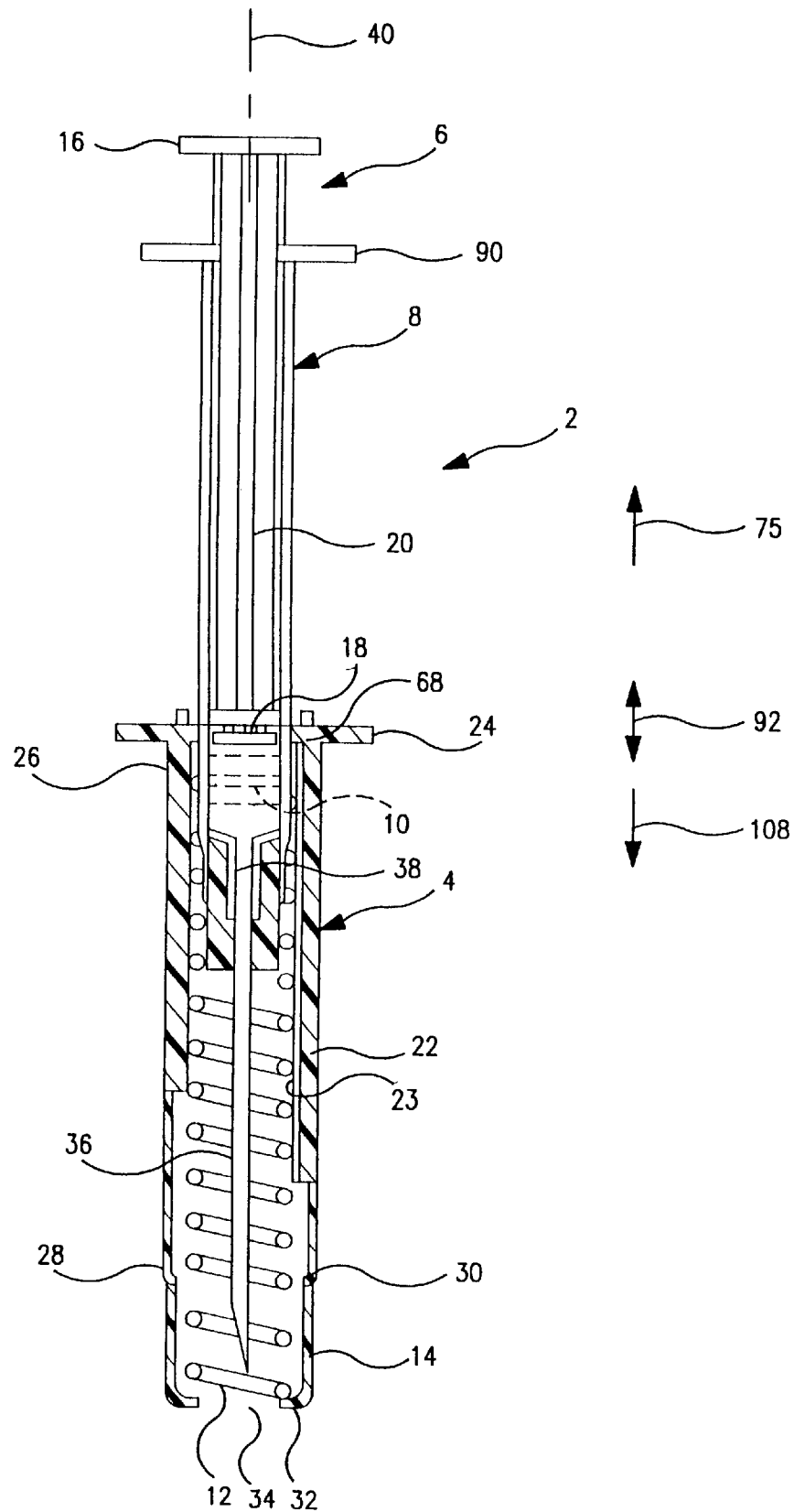
FIG. 1a is an elevation sectional view of the syringe of FIG. 1.
Figure 4:
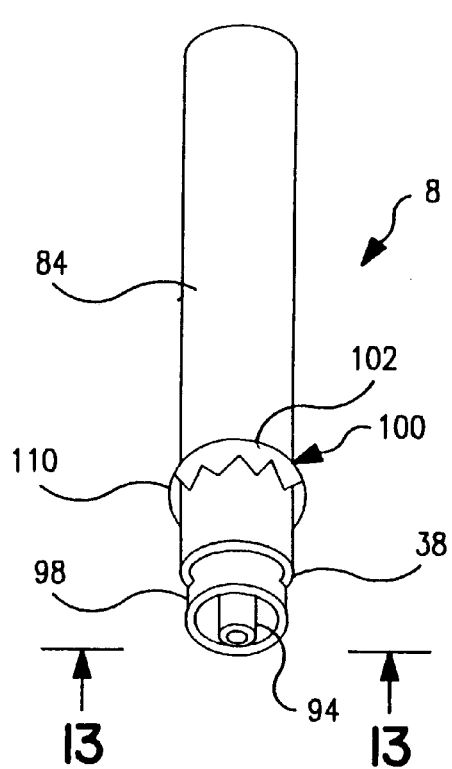
FIG. 4 is an isometric view of a vial used in the embodiment of FIG. 1.

(FIG. 1a). The needle assembly 36 is protected by a casing 15 which is later removed after the needle assembly 36 is attached to the vial 8.

The plunger 6 has a finger gripping flange 16 and a circular cylindrical sealing flange 18 connected by a ribbed shaft 20. The housing 4, FIG. 1a, includes a circular cylindrical body 22 with a circular cylindrical bore 23, a finger gripping flange 24 at the proximal end 26 and cap 14 at the body distal end 28. The cap 14 is welded to the body 22 at joint 30. The cap 14 has a radially inwardly depending flange 32 defining a needle receiving opening 34. Needle assembly 36 is releasably secured to the vial 8 at the vial distal end 38.

Figure 14:
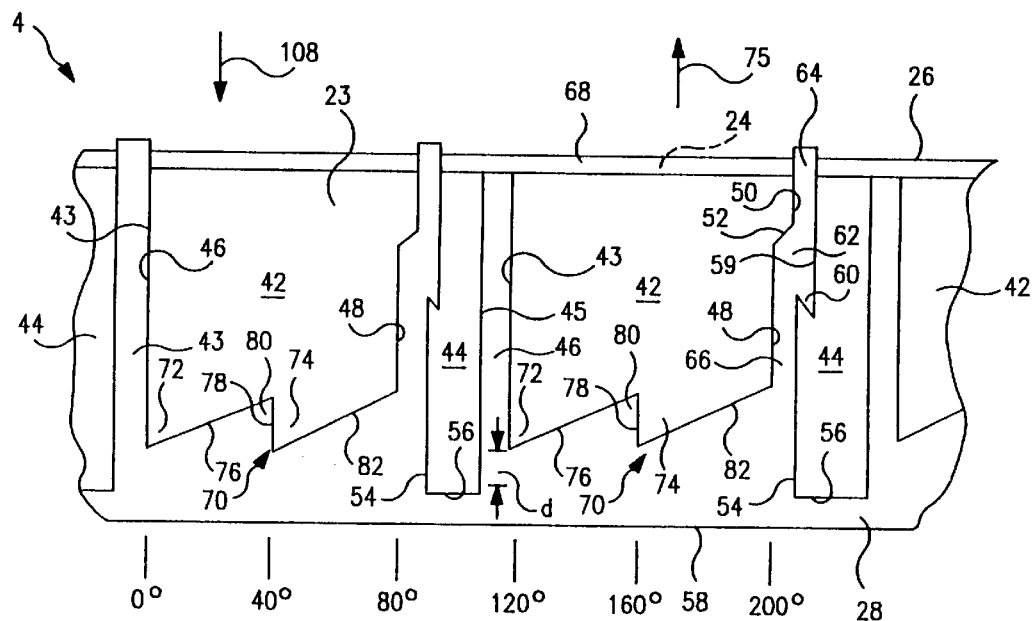
FIG. 14 is a fragmentary side elevation flattened view of the interior of the housing showing vial guide grooves for guiding the vial during axial positioning, positioning ratchet teeth for positioning the vial extended and a locking groove for locking the vial in the retracted position.

A portion of the housing 4 bore 23, FIG. 14, is shown flattened. Molded into the interior wall of the housing in the bore 23 are raised, i.e., radially inwardly extending, segments 42 and 44 extending in an axial direction along axis 40 (FIG. 1a). Two identical sets of segments 42 and 44 are shown, the bore being formed with three such identical sets. The segments 42 and 44 at one pair of facing spaced edges 43 and 45, respectively, form a linear axially extending groove 46.

The segment 42 on its opposing side has axially extending distal linear edge 48 coupled to axially extending proximal linear edge 50 by ramp edge 52. Edge 52 is inclined from edge 48 to edge 50 relative to the axial direction in a direction toward segment 44 and toward the proximal end 26.

The segment 44 has a first linear axially extending edge 54 terminating at one end edge 56 adjacent to, but spaced from the bottom edge 58 of the housing 4, edge 58 forming the cap 14 joint 30 (the cap 14 not being shown in this figure). The segment 44 has a linear axially extending second edge 59 spaced further from edge 48 than edge 50. The edges 54 and 59 are connected by a reverse edge forming a V-shaped notch 60. Groove 64 is formed by edges 50 and 59 and groove 66 is formed by edges 48 and 54. The notch 60 is spaced from the ramp edge 52 in the distal direction. This spacing forms an inclined groove 62 connected to axially extending equal width grooves 64 and 66.

The groove 64 extends through the flange 24. The segments 42 and 44 each terminate at the proximal end at radially inwardly depending flange 68 through which grooves 64 pass and at which grooves 46 terminate. The grooves 46, 64 and 66 are the same in transverse width between the adjacent edges. The scale of FIG. 14 is not in proportion to an actual device in the interest of clarity of illustration. In practice, the grooves and segments 42 and 44 may be narrower and longer than the proportion shown.

The segment 42 has a distal edge 70 which is in the form of saw tooth ratchet teeth 72 and 74. Tooth 72 has an edge 76 which is inclined toward the proximal end 26 and toward the edge 48 preferably about 45°. The tips of the teeth 72 and 74 are equally spaced a distance d in the proximal axial direction 75 from the next adjacent segment 44 edge 56. Tooth 74 has the same configuration as tooth 72. Tooth 74 has an axially extending linear edge connected to the edge 76 forming a V-shaped tooth root trough 80 therebetween. The tooth 74 has an inclined edge 82. Edge 82 intercepts edge 48 and is thus coupled to groove 66. The edge 76 is coupled to groove 46. The grooves 46 serves as guides for the vial as will be explained.

Figure 2:
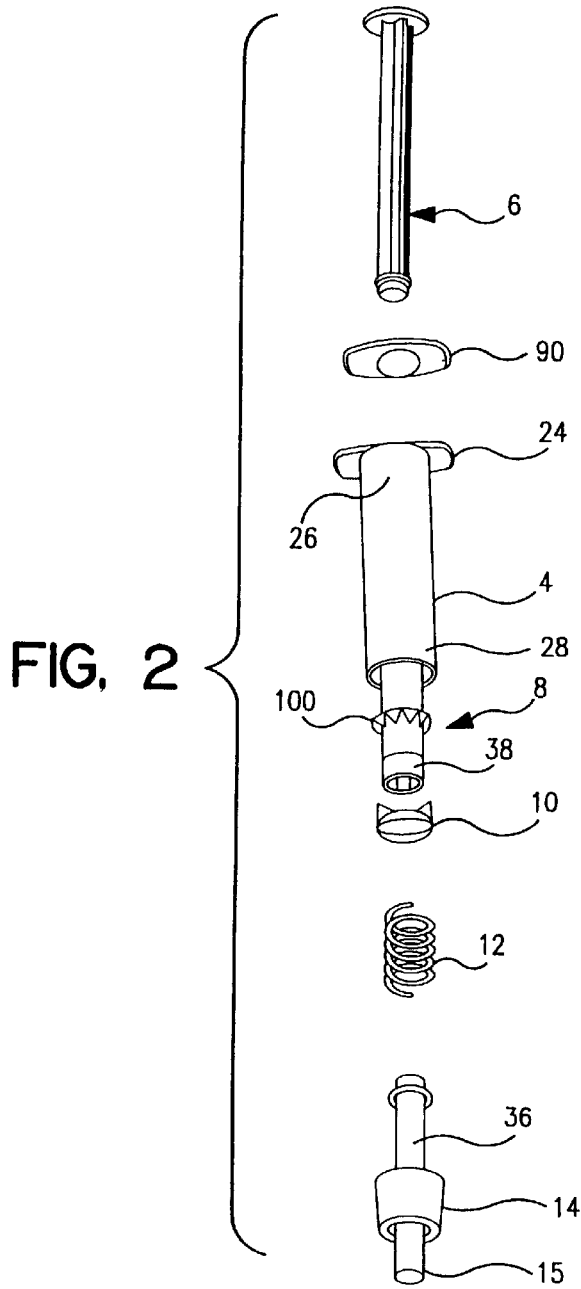
FIG. 2 is an exploded view of the syringe of FIG. 1.
Figure 5:
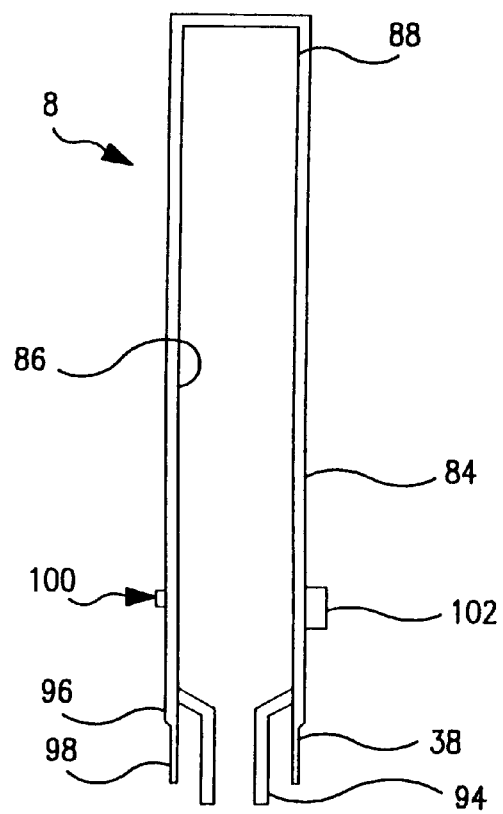
FIG. 5 is a sectional elevation view of the vial of FIG. 4.
Figure 6:
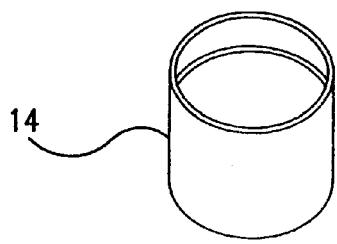
FIG. 6 is an isometric view of an end cap used in the embodiment of FIG. 1.

In FIG. 5, the vial 8 has a cylindrical body 84 forming a cylindrical cavity 86. The body 84 has a proximal end 88 to which an end flange member 90, FIG. 2, is welded after the vial is inserted into the housing 4 bore 23 (FIG. 1a) through the bottom distal end of the bore 23. The flange member 90 captures, with other structure to be described, the vial 8 in the housing 4 bore 23 for axial displacement in the bore in directions 92. In FIG. 5, the vial 8 has a needle assembly 36 receiving depending conical nozzle 94 molded to the body 84 in the cavity 86. The nozzle 94, preferably frictional, or threaded, in accordance with a particular implementation, releasably attaches the needle assembly 36 thereto. The body 84 has a radially inwardly stepped portion 98 at the body distal end.

In FIGS. 7 and 8, the vial 8 outer peripheral surface is molded integral with a one piece construction circular cylindrical ratchet member 100. Member 100 includes three annular equally spaced camming tabs 102, each being slidably received in a corresponding housing body groove 46 (FIG. 14). he tabs 102 each terminate at an upper distal edge at member 100 circular edge 104. Edge 104 abuts the flange 68 of the housing in the bore 23 in the retracted state of FIG. 1a. The tab 102, preferably about 0.060 inches in transverse width, has an inclined camming surface 106 facing the distal direction 108. A set 110 of ratchet teeth 112 are disposed between adjacent tabs, there being preferably three sets of tabs and three sets of teeth, equally spaced about the vial peripheral surface.

Figure 8A:
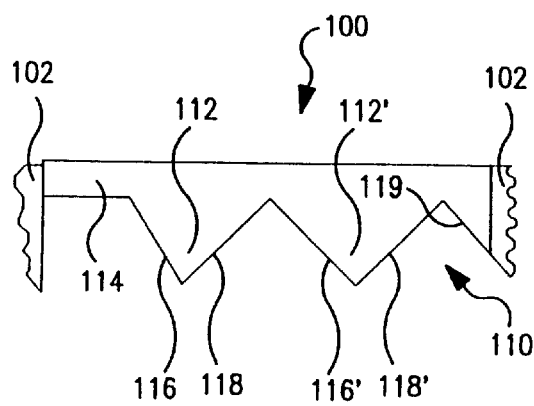
FIG. 8a is a fragmented flattened plan view of a portion of the ratchet teeth of the vial of FIGS. 7 and 8.
Figure 10:
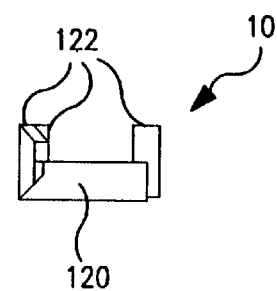
FIGS. 10–12 are respective elevation views of the ring of FIG. 9 taken along lines 10—10, 11—11 and 12—12.
Figure 11:
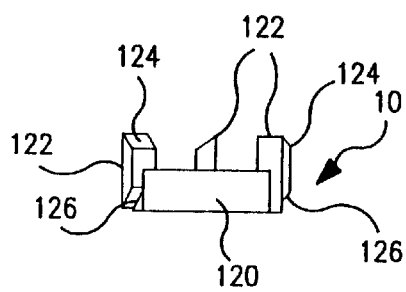
Figure 12:
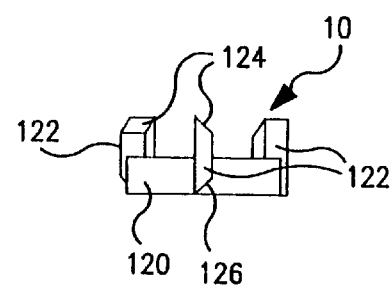
Figure 13:
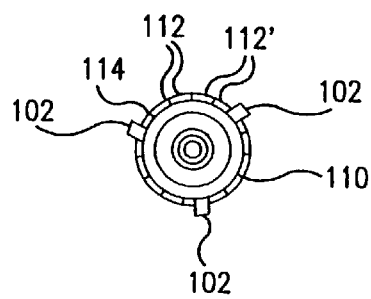
FIG. 13 is a bottom plan view of the embodiment of FIG. 4 taken along lines 13—13.

In FIG. 8a, a flattened view of the member 100 set 110, two teeth 112, 112' are each located in an angular segment of preferably about 40° spacing, with each tooth having a ramp camming surface in an angular 20° spacing, the teeth 112 being symmetrical with preferably about a 45° inclination to the axial direction. Each set 110 includes a circular annular peripheral rib member 114. Rib member extends between a tooth 112 and a tab 102. Each tooth 112, 112' has a pair of respective identical camming surfaces 116, 118 and 116', 118'. An inclined cam surface 119 is between surface 118' and a tab 102.

Ring 10, FIGS. 7–12, comprises an annular circular cylindrical ring member 120 and a set of three upstanding identical equally annularly spaced camming tabs 122. The tabs 122 function as pawls and selectively engage the ratchet teeth on the housing and on the vial. Each tab 122 has an inclined upper cam surface 124 and a lower inclined cam surface 126. The surfaces 124 and 126 are inclined in opposite directions. The surface 124 has an inclination that selectively mates with, abuts and is cammed by a corresponding ratchet member tab 102 inclined surface 106 and with the cam surfaces 119, 116' and 116 of the ratchet member 100 (FIG. 8a) teeth. The surface 124 also selectively mates with the edges 76 and 82 of the respective ratchet teeth 72 and 74 (FIG. 14) of the housing segments 42 and is cammed by these surfaces.

The ring 10 is molded separately form the vial 8 and is slidably and rotatably secured to the vial external peripheral surface. Preferably, the ring 10 is captured to the vial by the ratchet member 100 and a circular rib 128 (FIGS. 7 and 8) formed about the vial outer peripheral surface as by heat distortion of the vial body, for example. The ring 10 is free to rotate about the vial outer peripheral surface and to axial displace along that surface. The ring 10 axial displacement is sufficient so that the ring 10 tabs 122 can clear the tabs 102 of the ratchet member 100 to permit the ring 10 to selectively rotate about the axis 40. The tabs 122 are preferably the same transverse width as the tabs 102 and selectively slide within the grooves 46, 62, 64 and 66.

In operation, syringe 2 is assembled with the vial 8 in the retracted position of FIG 1a, with or without the needle assembly 38 attached. If not attached, the user attaches the needle assembly in a conventional manner. The needle in this position is fully enclosed by the housing 4 and is protected thereby from injuring personnel handling the syringe. The vial 8 is captured to the housing 4 by the ratchet member 100 and the flange member 90 which is attached by welding to the vial 8 proximal end after the vial is inserted into the housing bore 23.

Figure 15:
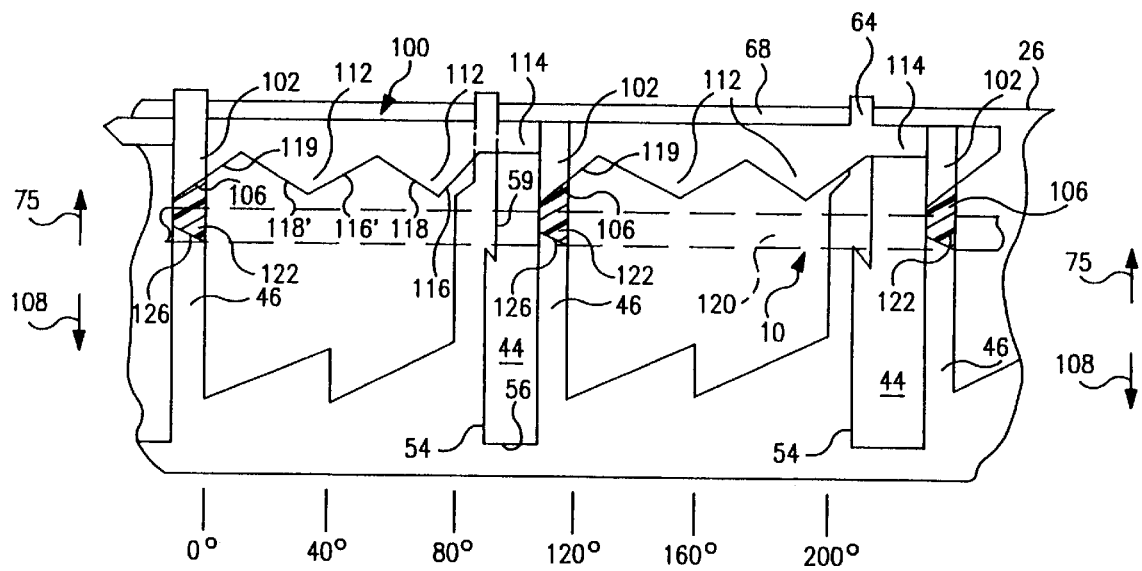
FIGS. 15–22 are views similar to the view of FIG. 14 showing the vial positioning cams in various position stages.

In use, the needle needs to be displaced from the housing 4 retracted position to an extended position, not shown. When extended the needle passes through the cap 14 opening 34 at the housing 4 distal end 28. In the initial retracted position of the needle, FIG. 15, the ring 10 tabs 122 inclined surfaces 124 each abut and mate with a corresponding camming inclined surface 106 of the ratchet member 100 tabs 102 in grooves 46. The spring 12 axially urges the vial 8 via the ring 10 in the proximal direction 75 with their respective tabs abutting. The tabs and groove 46 prevent the ratchet member 100 and ring 10 from rotating in this position, position 1. In this position, the upper edge 104 of ratchet member 100 abuts the flange 68.

Figure 16:
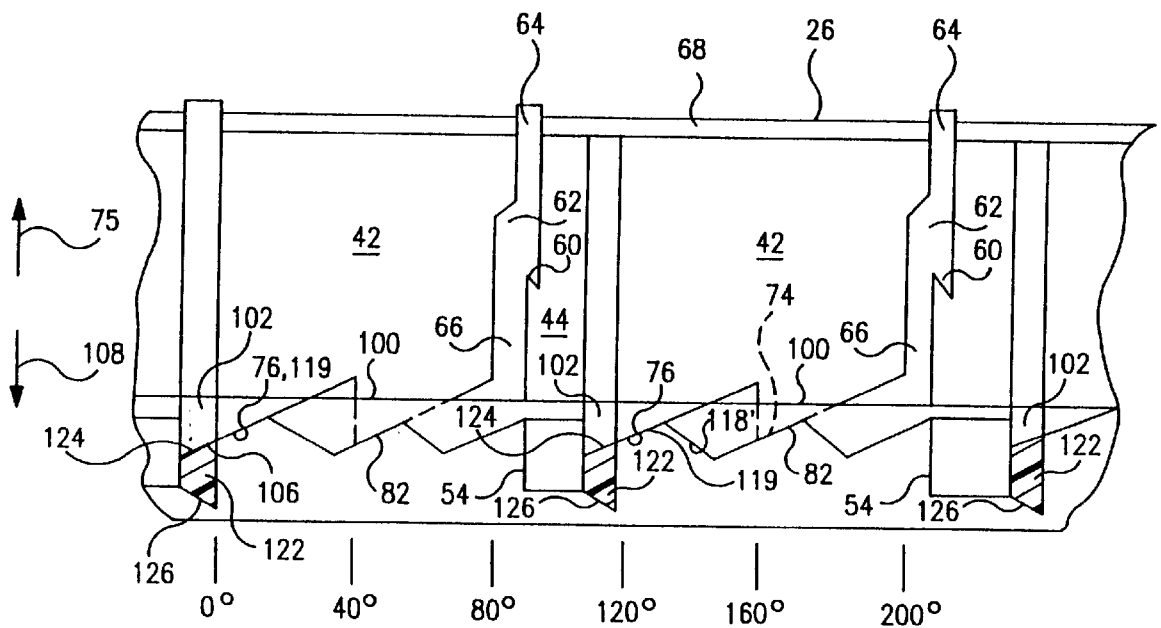

In FIG. 16, the vial is in a distal position. The vial is initially displaced to this position by pushing the plunger 6 and thus the vial 8 in direction 108 toward the housing distal end 28. It can also be placed in this position by pushing the vial at flange 90 axially in direction 108 in the absence of or in the presence of the plunger. The plunger 6 may be selectively inserted or removed from the vial cavity 86 as desired according to a given sequence.

As the vial reaches the extended position (not shown) corresponding to FIG. 16, the inclined surfaces 106 of the ratchet member 100 tabs 102 and surfaces 124 of ring 10 tabs 122 are placed coextensively aligned with the inclined surface 76 of teeth 72 of the housing segment 42.

Figure 17:
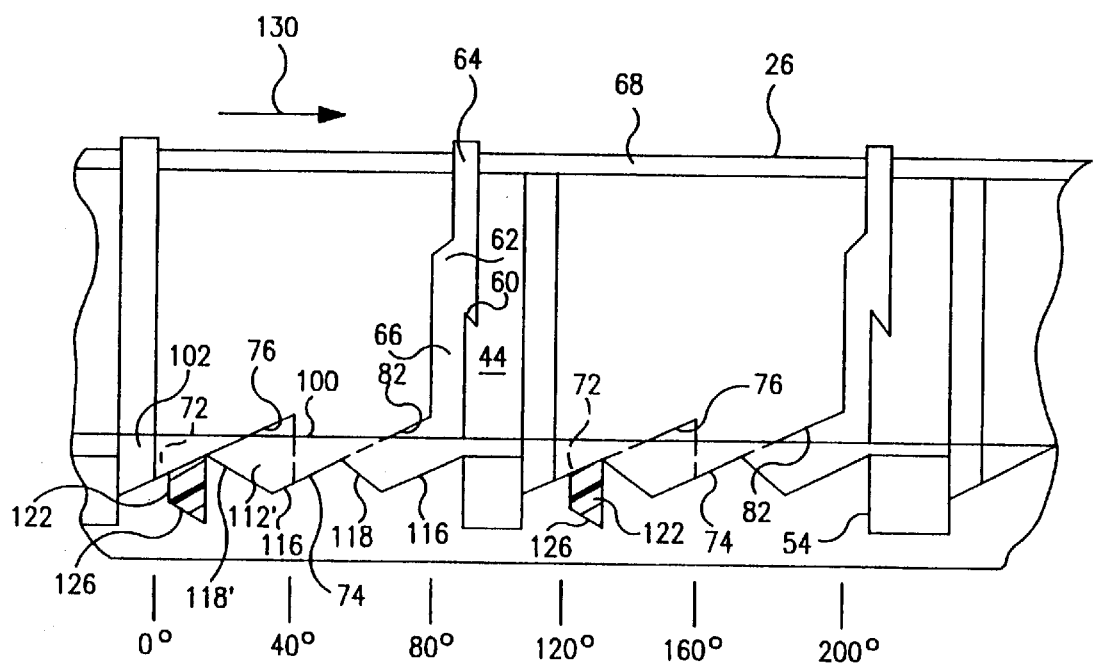

In this extended position, the spring 12 axial force on the ring 10 in direction 75 cams the ring 10 tabs 122 against the tabs 102 and teeth 72 inclined camming surfaces, rotating the ring 10 direction 130 to the position of FIG. 17. The ring 10 with its pawl tabs 122 cannot rotate further because of the restriction due to the ratchet member 100 ratchet teeth surfaces 118' and the abutting pawl formed by tab 122.

Figure 18:
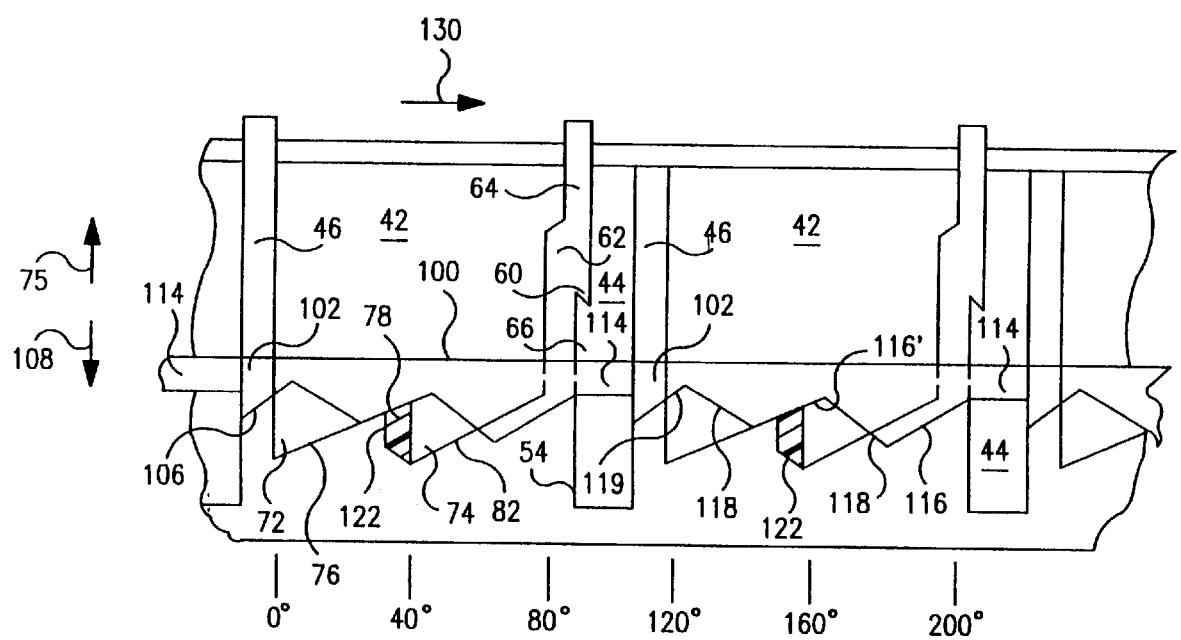

Upon release of the plunger, FIG. 18, however, with the spring 12 urging the ring 10 tabs 122 against the ratchet member 100 in the proximal direction 75, the vial 8 is displaced direction 75 to position 2. In this position, the vial is axially releasably locked in placed and ready for use. The tab 122 of ring 10 is locked against the tooth 74 edge 78 of the housing segment 42 in a ratchet-pawl arrangement and cannot rotate in direction 130 further. The needle is thus temporarily locked in this extended position. The plunger 6 is then used to place the desired fluid in the vial cavity 86 (FIG. 5) by withdrawing the plunger in direction 75 creating a vacuum in the vial cavity 86 as typical for syringes. The plunger is then depressed in direction 108 to inject the fluid in the normal procedure.

Figure 19:
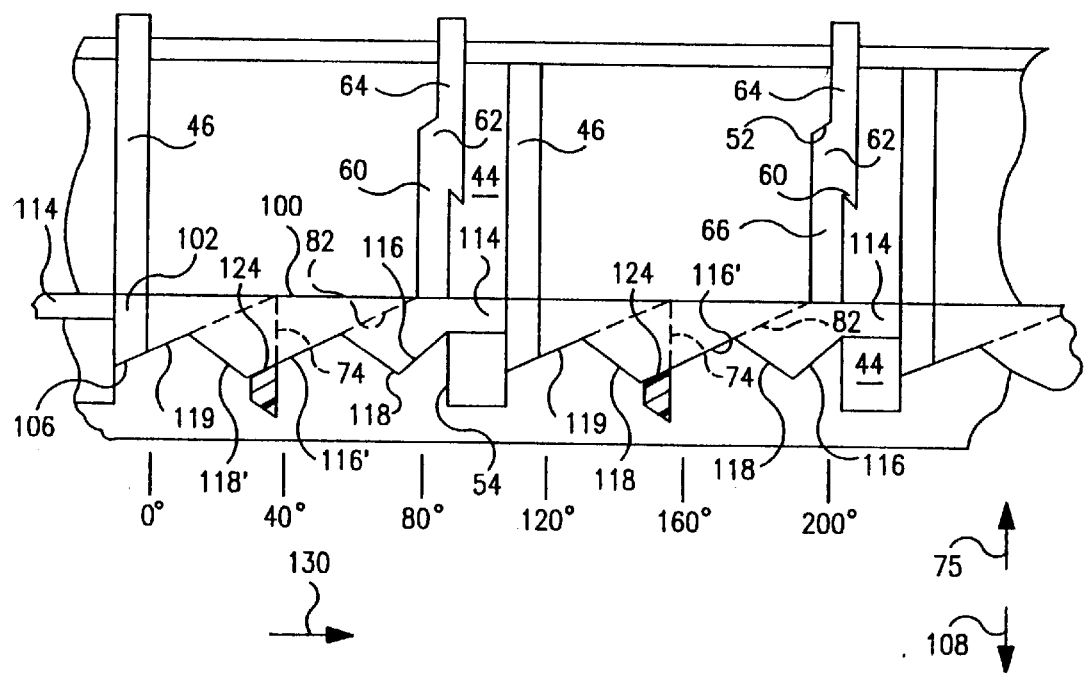

After the injection is completed, it is desired to retract the needle to preclude further use and to protect personnel from injury from the needle. To do this, the plunger 6 is depressed in the proximal direction 108 beyond the position 2 of FIG. 18 until the tab 122 of the ring 10 just passes the tip of the tooth 74 of the housing segment 42, FIG. 19. In this position, FIG. 19, the tab 122 surfaces 124 are aligned with the corresponding tooth 74 surfaces 82.

Figure 20:
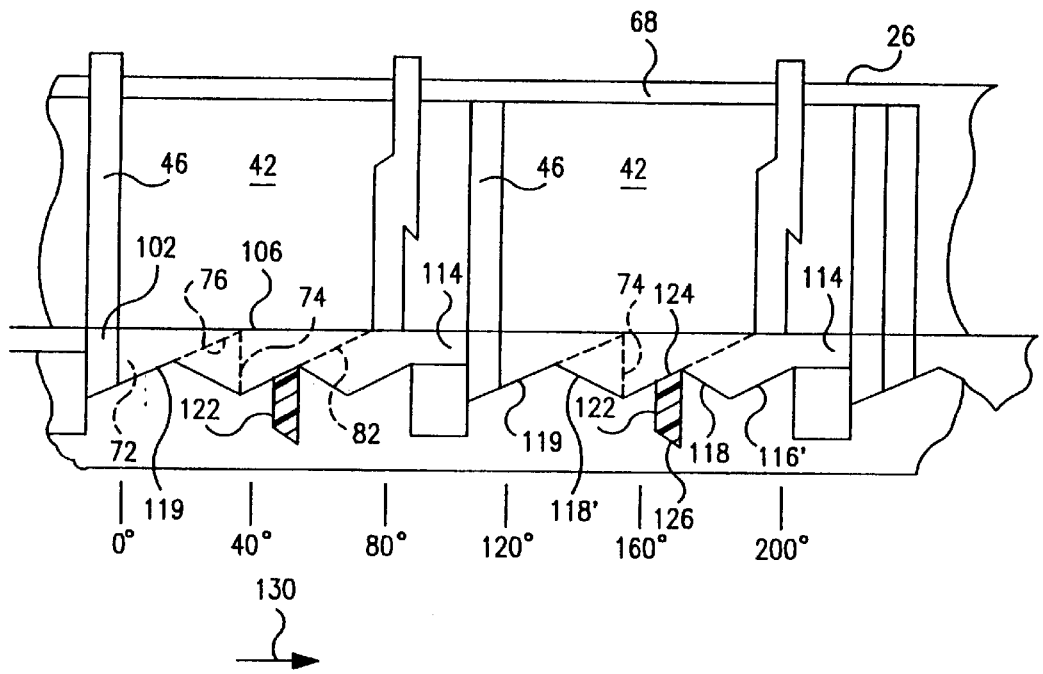

The spring 12 force in direction 75 on the ring 10 cams the ring tab 122 surface 124 against the tooth surface 116' of ratchet member 100 rotating the ring in direction 130 to the position of FIG. 20. At this time the vial 8 is free to retract and is retracted, automatically in direction 75, by the axial spring 12 force against the ring 10. The tabs 102 of the vial reciprocate in the grooves 46 guiding the vial in the axial direction 75 during this displacement, the vial 8 not rotating at any time.

It is also possible to end the injection with a partial injection of the fluid prior to emptying the vial 8. With the vial partially full of fluid, it is not desirable to displace the plunger 6 further to retract the vial as described above. This would further empty the vial. To immediately retract the vial and needle to its permanent locked protected position 3, the plunger may be removed from the vial. The vial 8 via its flange 90 may then be depressed in direction 108 relative to the housing 4 flange 24, with or without the plunger 6 present, further beyond the inject position 2, FIG. 18, at any time. This positions the vial 8 and attached needle assembly 36 in the sequence of FIGS. 19–22.

Figure 21:
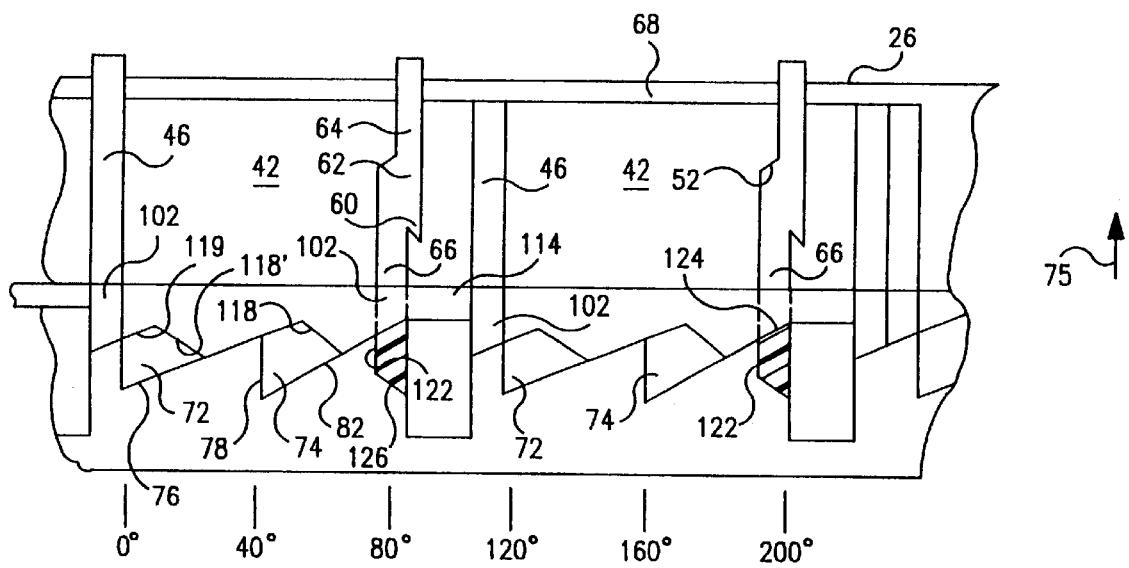

In FIG. 21, the axial spring 12 force on the ring 10 cams the ring via its pawl-like tabs 122 against the segment 42 tooth 74 edge 82 surface to position 3 aligned axially with groove 66. The spring force cams the tabs 122 in direction 130 against the camming surface 82 of teeth 74 until the tabs 122 snap against the respective edges 54 of the segments 44. The spring is continuously forcing the ring toward the proximal housing 4 end 26, direction 75. When the tabs 122 are aligned with the grooves 66, the ring 10 is now free to displace axially, direction 75, with the tabs 122 sliding in grooves 66. This forces the vial 8 in the same direction via its abutting tabs 102.

Figure 22:
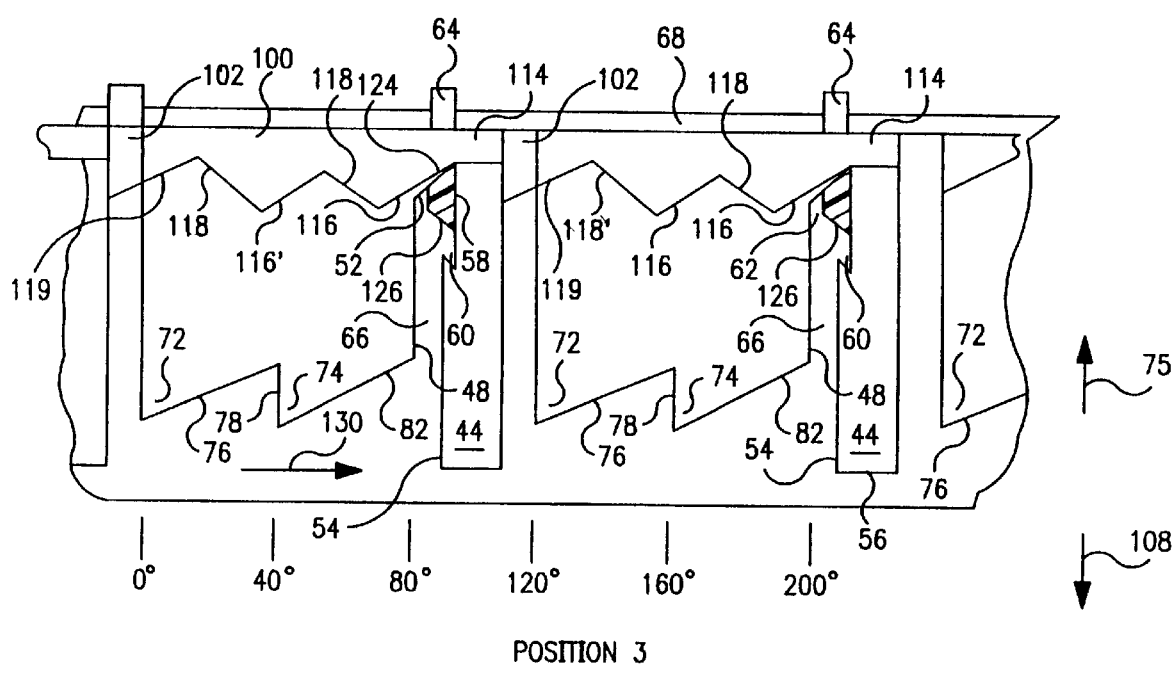

The ring 10 displaces in response to the spring force in direction 75, FIG. 22, until the tab 122 surface 124 engages the surface 52 of the groove 62. This surface 52 automatically cams the tab 122 into alignment with and along the groove 64 via inclined groove 62. The ratchet member 100 upper surface 104 at this time engages the lower surface of housing flange 68, which acts as a stop for the ratchet member 100 and, thus the vial 8, in direction 75 in the retracted position 3.

Should the user attempt to reuse the syringe 2 by depressing the plunger 6 in direction 108, the ring 10 V-shaped tabs 122 at the lower surface 126 enters the notch 160, axially and rotationally locking the vial in the retracted position. The notch 160 precludes the ring member from rotating in the direction opposite direction 130 precluding the alignment of the tabs 122 with corresponding grooves 66. Thus, the needle is permanently locked in the retracted position encased in the housing.

While three sets of segments and tabs are shown, this is by way of illustration. More or fewer may be provided in accordance with a given implementation. A minimum of two sets is preferred to provide a balance of the spring forces on the components. While the flange member 90 is shown rectangular, it may be other shapes. This member is preferably ultrasonically welded to the vial, but could be attached by other arrangements such as bonding and the like. The cap 14 is welded or otherwise attached to the housing 4 after the components are assembled to capture them to the housing bore 23.

While the ratchet member teeth are shown angular they may have other undulating shapes such as arcuate and the like. These shapes should match with the segment camming teeth shapes as described to achieve the desired camming action of the ring member 10. The camming surfaces of the tabs may have shapes other than inclined ramps, e.g., curved and so on.

It will occur to those of ordinary skill that modifications may be made to the disclosed embodiments. It is intended that the scope of the invention be defined by the appended claims.

What is claimed is:

1. A safety syringe for use with a needle comprising:
   a housing having a bore extending in an axial direction from a proximal housing end to a distal end;
   a vial in the housing bore having proximal and distal ends and a fluid receiving chamber for reciprocating displacement axially in the housing bore between retracted and extended positions, the distal vial end for securing the needle thereto in fluid communication with the chamber, said needle being fully retracted in the bore when the vial is retracted and extending from the bore when the vial is extended;
   resilient means for axially resiliently urging the vial to the retracted position;
   a plunger in the chamber for displacing the vial toward the distal end and for forcing fluid through the needle; and
   ratchet means coupled to the vial and housing bore for releasably securing the vial in the extended position in response to the vial being displaced in a first displacement to the extended position from an initial retracted position and for releasing the vial to retract to a second retracted position in response to said urging and to the vial being axially displaced in a second displacement toward the bore distal end.

2. The device of claim 1 wherein the ratchet means comprises ratchet teeth fixed to the housing in the bore and ratchet teeth fixed externally to the vial and a pawl with a pawl camming surface rotatably secured to the vial, said resilient means for resiliently urging the pawl in selective engagement with said vial ratchet teeth and with said housing ratchet teeth in response to said axial displacements of the vial to the bore distal end.

3. The device of claim 2 wherein the ratchet means includes a tab fixed to the vial with a first cam surface, the housing bore having first and second axial grooves, one of the grooves for axially guiding the tab during the vial displacement, the pawl rotatably secured to the vial having a second cam surface, the pawl being in the one groove in the initial retracted position and being cammed into engagement with said vial ratchet teeth and with the housing ratchet teeth by the engagement of the tab first cam surface with said pawl camming surface.

4. The device of claim 3 wherein the vial ratchet teeth cam the pawl out of engagement with the housing ratchet teeth in the extended position into engagement with the second groove for retracting the vial to the second retracted position in response to said urging.

5. The device of claim 4 including tab and pawl locking means coupled to the second groove at the housing bore proximal end for permanently automatically locking the vial retracted.

6. The device of claim 5 wherein the locking means comprises a slot in the housing bore coupled to the second groove for receiving the tab and pawl and having a locking recess extending in the distal end direction to rotationally and axially secure the pawl therein to preclude axial displacement of the vial to the distal end.

7. The device of claim 3 including a plurality of said ratchet means circumferentially spaced about the vial periphery and about the bore and first and second grooves.

8. The device of claim 7 including at least two sets of said grooves and ratchet means.

9. The device of claim 7 including three sets of said grooves and ratchet means.

10. The device of claim 1 including vial guide means coupled to the vial and to the housing for axially guiding the vial.

11. The device of claim 3 wherein the ratchet teeth, pawl and tab camming surfaces comprise complementary surfaces.

12. The device of claim 1 including means secured to the vial and cooperating with said housing for capturing the vial to the housing.

13. The device of claim 1 wherein the ratchet means comprises first and second ratchet teeth on the housing facing the distal bore end, first and second axially extending grooves in the housing wall in the bore on opposite sides of the ratchet teeth, a guide tab on the vial engaged with the first groove and having a first cam surface, a plurality of ratchet teeth on the vial outer surface facing the bore distal end, a ring member rotationally secured and axially captured to the vial outer surface for limited axial movement relative to the vial, a pawl secured to the ring member with a second cam surface for selectively engaging and responsive to the tab first cam surface and to the ratchet teeth, said pawl being in the first groove in the initial retracted position of the vial, said pawl being responsive to said resilient urging and displacement of said first cam surface for rotating and engaging the ratchet teeth when axially aligned with the ratchet teeth upon vial displacement to the distal bore end.

14. The device of claim 13 wherein the pawl in response to the second axial displacement is rotationally cammed by the vial ratchet teeth out of engagement with the housing ratchet teeth and into engagement with the second groove.

15. The device of claim 13 wherein the resilient member is a compression coil spring captured between the housing at the distal bore end and the ring member.

16. A safety syringe for use with a hollow needle comprising:
   a housing having a cylindrical cavity extending in an axial direction from a proximal housing end to a distal end;
   a cylindrical vial in said cavity and having proximal and distal ends and a fluid chamber for reciprocating axially in the cavity, the distal vial end for securing the hollow needle in fluid communication with the chamber, said vial for placing the needle in an extended position and in a retracted position;
   a plunger in the chamber passing through the vial proximal end for displacing the vial toward the distal end and for forcing fluid through the needle;
   a resilient member coupled to the housing and vial for urging the vial toward the proximal end; and
   cooperative cam means secured to the housing in the cavity and to the vial for axially releasably securing the needle in the extended position external the cavity in response to an initial vial displacement from the needle retracted position within the cavity to the needle extended position external the cavity, and for causing the vial and needle to automatically displace to the needle retracted needle position in the cavity in response to the vial being axially displaced toward the distal end from the extended position.

17. The syringe of claim 16 wherein the cooperative cam means comprises at least one cam surface on an interior surface of said housing in the cavity and at least one cam surface on the vial.

18. The syringe of claim 17 wherein the housing cavity has a wall with first and second spaced axially extending grooves, the at least one cam surface on the housing comprising an undulating surface extending circumferentially to the grooves facing the distal housing end and forming a trough medially the grooves, the at least one cam surface on the vial comprising an undulating surface facing in the same axial direction as the at least one cam surface on the housing, and pawl means movably secured to the vial for selective axial displacement in one groove at a time and for selective rotation about the vial in response to selective engagement with said at least one cam surface on the vial, said housing cam surface trough cooperating with the pawl means for selectively retaining the vial in a needle extended position, one of said grooves for receiving the pawl means in response to further axial displacement of the vial and for permitting the vial to retract to the retracted position.

19. A safety syringe for use with a hollow needle comprising:

a housing having proximal and distal ends and a cylindrical cavity defining an axis, said housing in the cavity including a plurality of radially inwardly extending ribs each extending in an axial direction and terminating adjacent to the proximal and distal ends of said housing and forming a medial rib spaced from two oppositely disposed adjacent outer ribs, the medial rib being spaced from the two oppositely disposed adjacent outer ribs by a corresponding longitudinally axially extending groove forming first and second spaced grooves and terminating a distance further from the distal end than the outer ribs, the medial rib terminating at a peripheral edge in communication with each said grooves, said edge comprising an undulating cam surface extending toward said distal end and defining a medial trough extending to the proximal end;

a cylindrical vial in the cavity for axially reciprocating in said cavity and having a chamber for receiving a liquid to be dispensed, said vial having a proximal end and a distal end for securing the hollow needle thereto in fluid communication with said chamber and for selectively passing the hollow needle through the housing distal end, said vial including a radially outwardly extending first tab with a first inclined cam edge facing the vial distal end for selectively axially displacing in said first groove from a needle retracted position at said housing proximal end to a needle extended position at said housing distal end, said vial including a second undulating cam surface defining at least one further trough medially therein extending axially to the vial proximal end, said needle in the retracted position being enclosed by said housing;

a ring member captured radially externally to and at the vial distal end for limited axially displacement along the vial and free to rotate about the vial, said ring member being intermediate the vial distal end and said first tab and second cam surface, said ring member including a radially outwardly extending second tab with a second inclined cam edge, said second tab being initially in said first groove with the second inclined cam edge facing and engaged with the first inclined tab edge, said second tab for selective cooperative engagement with said housing camming surface and with said vial camming surface when axially aligned therewith;

an axial displaceable plunger in the vial chamber for selective displacement of a fluid through said needle; and a resilient member secured in the housing cavity for resiliently urging the ring member and vial toward said housing proximal end and toward said vial cam surface such that in a normal quiescent state the resilient member urges the ring member second tab in the first groove against the vial first tab for displacing the vial to the retracted position;

upon initial axial displacement of the vial to the distal end, said first tab and resilient member cooperatively urging the second tab into engagement with the housing and vial cam surfaces when axially aligned therewith for cooperatively camming the second tab to the medial trough of the housing cam surface for releasably securing the needle extending from said housing cavity;

upon further axial displacement of the vial to the distal end, the vial cam surface engaging the second tab which cooperate with the resilient member for dislodging the second tab from the housing cam surface intermediate trough into the second groove whereby said resilient member automatically retracts said vial to the proximal end for retracting the needle into said cavity.

20. The device of claim 19 including a plurality of identical sets of said ribs, undulating cam surfaces and first and second tabs circumferentially spaced about the axis.

21. A safety syringe for use with a needle comprising:

a housing having a bore extending in an axial direction from a proximal housing end to a distal end;

a vial in the bore and having proximal and distal ends and a fluid receiving chamber for axial reciprocating displacement in the bore between retracted and extended positions, the distal vial end for securing the needle thereto in fluid communication with the chamber, said needle being fully retracted in the bore when the vial is retracted and extending from the bore when the vial is extended;

a resilient member coupled to the housing and vial axially resiliently urging the vial to the retracted position;

a plunger releasably secured in the chamber for selectively displacing the vial toward the distal end and for forcing fluid in the vial through the needle; and releasable positioning means for releasably locking the vial in the extended position upon initial axial displacement of the vial to the extended position, and for unlocking the vial upon a subsequent axial displacement of the vial toward the distal end beyond the extended position, and for displacing the plunger and vial to the retracted position in response to said unlocking and for permanently locking the vial in the retracted position.

22. The device of claim 21 wherein said positioning means includes cam means secured to the vial and housing bore responsive to the axial position of the vial in the bore for causing said releasable locking, unlocking and permanently locking.

23. The device of claim 22 wherein said cam means comprises cooperative ratchet and pawl means.

24. The device of claim 23 wherein the ratchet and pawl means includes ratchet teeth on the housing in the bore, a pawl rotatably secured to the vial for releasable engagement with the housing teeth and ratchet teeth on the vial for selective engagement and camming displacement of the pawl relative to said housing and vial ratchet teeth during said initial and subsequent axial displacements.

25. A safety syringe for use with a needle comprising:

a housing having a bore extending in an axial direction from a proximal housing end to a distal end;

a vial in the bore and having a fluid receiving chamber for receiving a plunger and having proximal and distal ends, said vial for axial displacement in the housing bore between retracted and extended positions, the distal vial end for securing the needle thereto in fluid communication with the vial chamber, said needle being fully retracted in the bore when the vial is retracted and extending from the bore distal end when the vial is extended;

resilient means coupled to the housing and vial for resiliently urging the vial to the retracted position; and positioning means responsive to an initial vial axial displacement for releasably locking the vial in the extended position, said positioning means for unlocking the vial upon a subsequent axial displacement of the vial toward the distal end and for displacing the vial to the retracted position in response to said unlocking.

26. The syringe of claim 25 wherein the initial and subsequent displacements are in the same axial direction.

27. The syringe of claim 25 wherein the vial has a first finger grasping flange and the housing has a second finger grasping flange, said first flange for displacing toward the second flange in said initial and subsequent displacements.

28. The syringe of claim 25 including means at the retracted position for permanently and automatically locking the vial retracted.

* * * * *